(12) United States Patent
Palepu

(10) Patent No.: US 8,815,833 B2
(45) Date of Patent: Aug. 26, 2014

(54) STABLE AMIFOSTINE LIQUID CONCENTRATE

(75) Inventor: Nageswara R. Palepu, South Hampton, PA (US)

(73) Assignee: Seidose, LLC, Amherst, MA (US)

( * ) Notice: Subject to any disclaimer, the term of this patent is extended or adjusted under 35 U.S.C. 154(b) by 1011 days.

(21) Appl. No.: 11/983,340

(22) Filed: Nov. 8, 2007

(65) Prior Publication Data

US 2008/0139515 A1    Jun. 12, 2008

Related U.S. Application Data

(60) Provisional application No. 60/857,823, filed on Nov. 9, 2006.

(51) Int. Cl.
*A61K 31/66* (2006.01)
*C07F 9/165* (2006.01)

(52) U.S. Cl.
USPC .......................................... 514/114; 558/166

(58) Field of Classification Search
None
See application file for complete search history.

(56) References Cited

U.S. PATENT DOCUMENTS

| | | | |
|---|---|---|---|
| 5,424,471 A | 6/1995 | Kennedy et al. | |
| 5,591,731 A | 1/1997 | Kennedy et al. | |
| 5,994,409 A | 11/1999 | Stogniew et al. | |
| 6,384,259 B1 * | 5/2002 | Stogniew et al. | 558/146 |
| 6,407,278 B2 | 6/2002 | Stogniew et al. | |
| 6,489,312 B1 * | 12/2002 | Stogniew et al. | 514/109 |
| 6,841,545 B2 | 1/2005 | Stogniew et al. | |
| 7,060,708 B2 | 6/2006 | Piccariello et al. | |
| 2005/0209200 A1 | 9/2005 | Stogniew et al. | |

FOREIGN PATENT DOCUMENTS

| | | |
|---|---|---|
| WO | 02/18396 | 3/2002 |
| WO | 03/026570 | 4/2003 |

OTHER PUBLICATIONS

Remington's Pharmaceutical Sciences, pp. 420-425, 1980.*
Risley et al ("Hydrolysis of S-2-(3-aminopropylamino)ethylphosphorothioate (WR-2721)" Biochemical Pharmacology. 1986; 35(9):1453-1458).*
Merck Index Entry for Amifostine; Merck Index 14th edition, 2006; Entry # 404, p. 69.
Piper, et al; S-2-(omega-aminoalkylamino)ethyl Dihydrogen Phosphorothioates and Related Compounds as Potential Antiradiation Agents. J med Chem Mar. 1969 vol. 12, 236-243.

* cited by examiner

*Primary Examiner* — Timothy Thomas
*Assistant Examiner* — Rayna B Rodriguez
(74) *Attorney, Agent, or Firm* — Irving M. Fishman

(57) ABSTRACT

A storage stable aqueous solution of amifostine at a pH of at least 10.0, in an amifostine concentration of about 50 to about 250 mg/l, which formulation is storage stable under refrigerated conditions.

11 Claims, No Drawings

STABLE AMIFOSTINE LIQUID CONCENTRATE

CROSS-REFERENCE TO RELATED APPLICATIONS

This application claims the benefit of priority from U.S. Provisional Application Ser. No. 60/857,823, filed Nov. 9, 2006, the contents of which are incorporated herein by reference.

STATEMENT REGARDING FEDERALLY SPONSORED RESEARCH OR DEVELOPMENT

Not Applicable

FIELD OF THE INVENTION

The present invention relates to amifostine and storage stable liquid concentrates thereof, particularly aqueous liquid concentrates thereof. The invention further relates to methods of manufacture of such stable liquid concentrates.

BACKGROUND OF THE INVENTION

Amifostine is a phospho ester compound that is used pharmacologically for the amelioration of side effects of radiation and chemotherapy. The compound is currently marketed as a lyophilizate of a crystalline trihydrate of amifostine, typically in vials of 500 mg, which is reconstituted to a final administration concentration of 5 to 40 mg/ml for IV infusion. Reconstitution procedures leave room for the possibility of not really dissolving all of the lyophilizate and therefore potentially underdosing the patient in question, a result which does not frequently occur, but is unacceptable when it does. Amifostine is known to undergo hydrolysis in aqueous solution at acidic, neutral, and mild basic conditions. Thus, it was believed that stable aqueous formulations that would not hydrolyze to any appreciable extent over typical storage time periods were not likely to be found. Furthermore, the aqueous solubility of amifostine trihydrate in water is about 200 mg/ml at ambient conditions, and further, when such a solution is stored at refrigerated conditions to thermodynamically limit the hydrolysis, substantial crystallization results. In addition, because of limited refrigeration space, kinetic and neutralization/dilution considerations, substantially less concentrated concentrates are not suitable either since they take up additional space and the lesser the concentration, the less stable the concentrate. Thus, aqueous liquid concentrates of amifostine were simply thought not possible. Because such an aqueous liquid amifostine concentrate would eliminate a potential source of dosing errors in clinical practice, there is clearly a need for the same.

There are four $pK_a$s for amifostine. The Merck Index lists them to be <2.0, 4.2, 9.0 and 11.7. The amino groups (2) and the phosphate group (2 pKa per group) can all be completely protonated. [Ref: Structure of Radio protective agent S-2(3-Aminoprpropylamino)ethylphosphorthioic acid (WR 2721) Jean Karle, Acta Cryst (1988) C44 135-138]. The usual form crystallized from solution is a double zwitterion with the phosphate completely dissociated (−2) and the amino groups fully protonated (+2). It is usually drawn with the amines in their free base form and the phosphate completely protonated but that is not how it exists in solution. So, the two $pK_a$ values from the double zwitterion are for the two amino functions ionizing (i.e., $pK_a$s 3 & 4). The first two $pK_a$s are for the phosphate which are perturbed by the two positive charges on the amino groups which pushes them lower than $pK_a1$ and $pK_a2$ for phosphoric acid. The following table describes the ionic nature of the compound as function of pH according to the $pK_a$ values reported in the Merck Index. The table also summarizes the approximate concentration of ionic species as function of pH:

| | | | $pK_a$ | | | |
|---|---|---|---|---|---|---|
| pH | $pK_a$ <2.0 | $pK_a$ 4.2 | $pK_a$ 9.0 Prim. amine Protonated | $pK_a$ 9.0 Prim. amine Unprotonated | $pK_a$ 11.7 Sec. amine Protonated | $pK_a$ 11.7 Sec. amine Unprotonated |
| 7 | $PO_3$ (−) | $PO_3$ (−) | ~100% (+) | ~0% | ~100% (+) | ~0% |
| 9 | $PO_3$ (−) | $PO_3$ (−) | ~50% (+) | ~50% | ~100% (+) | ~0% |
| 10 | $PO_3$ (−) | $PO_3$ (−) | ~10% (+) | ~90% | ~100% (+) | ~0% |
| 11 | $PO_3$ (−) | $PO_3$ (−) | ~1% (+) | ~99% | ~83% (+) | ~17% |
| 12 | $PO_3$ (−) | $PO_3$ (−) | ~0.1% (+) | >99.9% | ~33% (+) | ~67% |
| 13 | $PO_3$ (−) | $PO_3$ (−) | ~0.01% (+) | 99.99% | <5% (+) | >95% |

With increasing pH, the concentration of the amine free base increases for both amine functions. For example, at pH 11 the primary amine with $pK_a$ 9 is predominantly present as the free base form. At pH 13, both primary and secondary amines are predominantly present as their free base forms.

OBJECTS OF THE INVENTION

It is therefore an object of the invention to provide an aqueous, storage stable amifostine liquid formulation.

It is another object of the invention to provide an aqueous, storage stable amifostine liquid concentrate formulation under refrigerated conditions, i.e. at temperatures of less than about 10° C.

It is still another object of the invention to provide a method of obtaining such a storage stable aqueous liquid formulation of amifostine.

Still other objects of the invention will be apparent to those of ordinary skill in the art.

BRIEF SUMMARY OF THE INVENTION

These and other objects of the invention are surprisingly achieved by preparing an aqueous solution of amifostine at a pH of at least 10.0, which is storage stable under refrigerated conditions for extended periods. Preferred aqueous solutions have amifostine concentrations of from about 50 to about 250 mg/ml. In preferred aspects of the invention, the amifostine formulation is stable, i.e. it retains at least about 90% of its activity for at least about 180 days, and more preferably about 270 days or longer when stored at a temperature of less than about 10° C., preferably from about >0° C. to about 10° C. and more preferably about 2° C. to about 8° C., even more preferably about 5° C. In preferred aspects of the invention, the amifostine formulation retains at least about 92% and in further preferred aspects of the invention, the amifostine formulation retains at least about 95% of the amifostine activity when stored at these temperatures and time frames.

The invention also includes kits containing the amifostine containing composition described herein as well as methods of treating various conditions, including those known to amenable to treatment with amifostine, such as without limitation, reducing (cumulative) renal toxicity in patients receiving chemotherapy and/or methods of reducing xerostomia in patients receiving radiation therapy to the head or neck, for example. The methods of treatment include providing a storage stable amifostine containing formulation as described herein, adjusting the concentration and pH of the formulation containing the aminofostine to a physiologically acceptable range suitable for direct administration to a patient in need thereof and administering a sufficient amount of the physiologically acceptable amifostine formulation to a patient in need thereof.

DETAILED DESCRIPTION OF THE INVENTION

The present invention is especially directed to aqueous, concentrated formulations of amifostine that are storage stable for extended periods under refrigerated storage conditions. Amifostine, when present as the free base with both protons on the phosphate ionized (i.e., deprotonated), has both greater stability as well as solubility than that of the corresponding forms at lower pH (i.e. less negative charge, especially lesser than net −1 charge). This is unusual because a free amine is usually more reactive in hydrolytic degradation than its protonated form.

As used herein, the statement that a formulation and or composition is "storage stable" means that at least about 90%, preferably at least about 92% and more preferably at least about 95% of the amifostine remains in the active (and not hydrolyzed) form, after about 90, 180, or 270 days, or even longer, when stored under refrigerated conditions, i.e. temperatures less than about 10° C., preferably from about >0° C. to about 10° C., more preferably from about 2 to about 10° C., yet more preferably about 3 to about 8° C., and still more preferably about 5° C. The term "refrigerated" conditions means substantially constant temperature and storage conditions within this range, that is, the concentrate remains in the temperature range for substantially the entire period between shortly (generally no more than a few hours) after manufacture and shortly (generally no more than a few hours) before further dilution for administration.

As used herein, the stability of a formulation provided herein refers to the length of time at a given temperature that is greater than 90%, 92% or 95% of the initial amount of active ingredient, e.g., amifostine, is present in the formulation. Thus, for example, a composition that is stable for 180 days at about 5*C would have at least 90%, preferably at least 92%, more preferably 95% of the initial amount of amifostine present in the formulation after 180 days following storage at about 5° C.

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there is a plurality of definitions for a term herein, those in this section prevail unless stated otherwise.

As used herein, a pharmacologically suitable fluid is a solvent suitable for pharmaceutical use. Exemplary pharmacologically suitable fluids include polar fluids, including protic fluids such as water.

The compounds produced may be administered to animals or humans and can be pharmaceutically active drugs or pro-drugs.

As used herein, treatment means any manner in which one or more of the symptoms of a condition, disorder or disease are ameliorated or otherwise beneficially altered. Treatment also encompasses any known pharmaceutical use of the amifostine-containing formulations described herein.

As used herein, treatment or amelioration of the symptoms of a particular disorder by administration of a particular pharmaceutical composition refers to any lessening, whether permanent or temporary, lasting or transient that can be attributed to or associated with administration of the composition.

In one aspect of the invention, the inventive amifostine-based formulations can be prepared as follows:

Amifostine, preferably crystalline trihydrate or monohydrate, is dissolved in an aqueous base having a pH in excess of 10.0, preferably not less than about 10.5, more preferably not less than about 11.0, more preferably not less than about 11.5. Higher pH solutions are also preferred, such as about 11.7, about 12.0, about 12.5, about 13.0, and about 13.5. When desired, amifostine as synthesized can be utilized from the mother liquor (thereby avoiding the use any particular solid amifostine starting material) by simply adding sufficient base to make the solution within the pH limitations of this paragraph. Any aqueous base that is sufficiently basic to achieve the desired pH and is acceptable to be administered by IV infusion (at lower pH) is acceptable for the present invention. Such basic compounds include NaOH, arginine, lysine and other amino acids with basic pKa is >9.5. The amount of amifostine included in the inventive formulations is described in detail below, but will generally be about 250-260 mg/ml or less.

For purposes of this description, the amifostine amine group with a $pK_a=9$ is designated as amine 1 and the amifostine amine group with a $pK_a=11.7$ is designated as amine 2. At pH 7.4, the intrinsic pH, amifostine has a net neutral charge as a double zwitterion with the phosphate completely dissociated (−2) and the amino groups fully protonated (+2). During stability evaluations carried out for the purposes of the present invention it was observed that the hydrolysis of amifostine to release free thiol metabolite is rapid at acidic pH and even at weakly acidic pH. On the other hand, the hydrolysis was almost 100-fold slower at pH 10 and above.

One aspect of the present invention involves the development of a concentrated solution of amifostine at pH 10 and above. For purposes of the present invention, "concentrated" shall be understood to include solutions of greater than about 50 mg/ml. Some preferred concentrated solutions in accordance with the present invention are set forth below but generally include those of up to about 250 mg/ml. The inventive formulations are preferably kept under refrigerated conditions yet the solutions are surprisingly stable for long periods of time when compared to similar amifostine-containing solutions which are kept at pH's below the pH 10 mentioned above, i.e. <9.5 or less basic pH's. There is no need to use the lyophilization process in order to provide amifostine formulations of the present invention having sufficient long term storage qualities. Indeed, the advantages of the formulations of the present invention are apparent when the patient package insert indicates that currently approved amifostine formulations after reconstitution at 50 mg/ml at physiological pH are stable for only 24 hours under refrigeration. Moreover, the reconstitution and under-dosing problems associated with the prior art lyophilized amifostine products are completely avoided.

As will be seen below in Example 1, a 250 mg/ml liquid concentrate was prepared at pH 9, and 200 mg/ml liquid concentrates were prepared at pH 10.5, 11.5, 12.5 and 13. The stability was monitored at 40° C., 25° C. and 5° C. by a stability indicating HPLC method using the following HPLC conditions:

Equipment:

| | |
|---|---|
| Chromatographic systems | Shimadzu LC-2010$C_{HT}$ with LC solutions Chromatographic PC based work station. |
| Electronic balance | AND, Model No. R202 (0.01 mg sensitivity) & Shimadzu AX200 (0.1 mg sensitivity) |
| Usual laboratory glassware | Class-A Volumetric flasks and pipette |

Standards and Solvents:

| | |
|---|---|
| Amifostine standard | Standardized known purity of Amifostine Trihydrate |
| Acetonitrile | HPLC grade (Rankem) |
| Water | Milli - Q (Millipore) |
| Nonafluoro Butane Sulfonic Acid | AR grade (Sigma Aldrich) |
| Tri Ethyl Amine (TEA) | AR grade (Rankem) |
| Ortho Phosphoric Acid | AR grade |

Method:

| | |
|---|---|
| a) Chromatographic system | Shimadzu LC-2010$C_{HT}$ with LC solutions Chromatographic PC based work station. |
| b) Column | Whatman-Partisil 10 ODS-1 250 × 4.6 mm ID and 10μ particle size |
| c) Mobile Phase | Buffer Preparation: Dissolve 1.0 ml of Nonafluoro butane Sulfonic acid in 1200 ml of HPLC Water. To this add 8 ml of TEA. Adjust pH to 7.5 using Ortho Phosphoric acid. Mobile Phase Preparation: Mobile Phase: Buffer:Acetonitrile 900:100 Degas the mobile phase. |
| d) Flow rate | 0.9 ml/min |
| e) Pump mode | Isocratic |
| f) Detection wavelength | 220 nm |
| g) Column Temperature | 30° C. |
| h) Injection Volume | 10 μL |
| i) Sample cooler | Ambient |
| j) Run time | 20 min. |
| k) Diluent | Mobile phase |

Below pH 10, under refrigeration conditions, a 200 mg/ml amifostine solution crystallizes out; the solubility of amifostine at 5° C. is about 100 mg/ml. At pH 9.0, 50% of the amifostine is present as the double zwitterion and 50% of amine 1 (primary amine) is present as the free base form making 50% of the amifostine have a net negative charge. At pH 10.0, only 10% of amifostine is present as a double zwitterion and the other 90% has a net negative charge; amine 1 is mainly in the free base form. Under refrigeration conditions, a 200 mg/ml amifostine solution at this pH remained clear with no crystallization observed. This surprisingly suggests that the double zwitterionic form is less soluble than ionic form where the net charge is −1. In pH 11.5 solution, amifostine is present as four ionic species as shown in the Table above. Approximately 1% is present as the double zwitterion. More importantly, 17% of amifostine has both amines in the un-ionized form as free bases and this particular ionic species of the molecule carries about −2 charge. At this pH (11), it is observed that there is a significant improvement in the stability. While Applicant is not bound by theory, it is believed that the free base form of amifostine as a −2 ion is more stable than the double zwitterion and the intermediate −1 charged form. At pH 13, over 95% of the amifostine is present with both amines in their free base forms with improved stability. It has therefore been surprisingly found that this free base form with a −2 charge has a better stability and solubility over the double zwitterion form and even over the −1 ionic form.

Since amifostine in solution is not limited to any particular crystalline or amorphous form or salt thereof, any of these forms of amifostine are suitable for preparing the present invention concentrates. However, the crystalline trihydrate has been shown to have a sufficient ease of dissolution and although non-crystalline material is generally easier to dissolve, solid non-crystalline material is generally not as stable as crystalline materials, so that on balance, crystalline materials are preferred. Crystalline amifostine trihydrate material is one of the more preferred forms of amifostine for use in preparing the instant invention concentrates as are crystalline anhydrous amifostine or crystalline amifostine monohydrate. As stated earlier, when desired, mother liquor having amifostine in solution can be used as the source of the amifostine whereby use of solid amifostine in the finished dosage from as a starting point is avoided.

In some aspects, the amifostine concentrates of the present invention are typically 50 mg/ml to about 250 mg/ml or higher. Preferably, they are from about 100 mg/ml to about 250 mg/ml. In alternative aspects of the invention, the amifostine concentrations are at least about 125 mg/ml, preferably at least about 150 mg/ml, more preferably at least about 175 mg/ml, yet more preferably at least about 200 mg/ml. In some still more preferable embodiments, the amifostine concentration is at least 225 mg/ml, and is yet more preferably at least about 250 mg/ml.

When utilized, the concentrate is diluted to a final concentration of about 5 to 40 mg/ml with water for injection or buffered water for injection if needed in order to bring the pH into the range that is acceptable for IV infusion, i.e. an IV injectably compatible diluent. When a buffered water for injection is needed or desired, hydrochloric acid solution, lactic acid solution or citrate buffer can be utilized, a particularly useful concentration of either of these is about 300 mmolar to about 800 mmolar, but other concentrations may be used as needed. In each of these diluents, a sufficient amount of tonicity agent may further be added to make the final infusion more physiologically acceptable. Thus, a lactated saline or citrated glucose solution may be utilized as may any other IV infusion compatible solutions of buffered or unbuffered tonicity agents. Typically, the concentrate is added to sufficient aqueous diluent, with or without allowing the concentrate to come to room temperature first. Allowing the concentrate to come to room temperature will insure that the amifostine does not precipitate in the course of lowering the pH; however, this is not critical and the concentrate can be added to the diluent while still cold. As will be appreciated by those of ordinary skill, the storage stable formulations of the present invention can also include any art-recognized pharmaceutically acceptable adjuvants and excipients necessary or desirable for commercial adaptation that do not contribute to or otherwise promote hydrolysis of the amifostine.

Once the concentrated solutions of amifostine are diluted and pH adjusted to physiologically acceptable levels, the resultant solution can be used in the treatment of any amifostine responsive condition or as a cytoprotective agent, including those currently acknowledged by those of ordinary skill.

Some preferred conditions include the treatment or reduction of cumulative renal toxicity associated with chemotherapy and in the treatment or reduction of moderate to severe xerostoma associated with radiation of the head and neck. The amount of amifostine administered will be apparent to the artisan of ordinary skill but can range in amount from about 50 to 1,000 mg/m².

In a still further aspect of the invention, there are provided kits containing a suitable pharmaceutically acceptable container containing a concentrated aqueous amifostine formulation having a pH of at least about 10 which is suitable for long term storage and instructions for storing the same under refrigerated conditions and optionally, directions for use in patients requiring treatment with amifostine.

EXAMPLES

Example 1

Solutions of amifostine at 200 mg/ml or 250 mg/ml were prepared at the pHs shown in the table below and stored at the temperatures indicated for the times indicated. "% remaining" in the table below is determined by the HPLC method described earlier in the specification.

| pH | Amifostine Concentration mg/ml | Storage Temperature °C. | Storage Time (Days) | % remaining |
|---|---|---|---|---|
| 7.4 | 250 | 40 | 1 | 84 |
| 7.4 | 250 | 40 | 2 | 66 |
| 7.4 | 250 | 40 | 3 | 57 |
| 7.4 | 200 | 40 | 2 | 71 |
| 7.4 | 200 | 25 | 7 | 89 |
| 7.4 | 200 | 25 | 14 | 78 |
| 7.4 | 200 | 25 | 25 | 60 |
| 7.4 | 200 | 25 | 33 | 52 |
| 9.0 | 250 | 40 | 1 day | 83 |
| 9.0 | 250 | 25 | 10 days | 83 |
| 9.0 | 250 | 25 | 25 days | 60 |
| 9.0 | 250 | 5 | 90 days | 96 |
| 9.0 | 250 | 5 | 180 days | 91* |
| 10.5 | 200 | 40 | 1 day | 84 |
| 10.5 | 200 | 40 | 2 days | 75 |
| 10.5 | 200 | 25 | 10 days | 85 |
| 10.5 | 200 | 25 | 25 days | 62 |
| 10.5 | 200 | 25 | 35 days | 57 |
| 10.5 | 200 | 25 | 60 days | 39 |
| 10.5 | 200 | 5 | 90 days | 94 |
| 10.5 | 200 | 5 | 180 days | 90 |
| 11.5 | 200 | 40 | 1 day | 90 |
| 11.5 | 200 | 25 | 10 days | 86 |
| 11.5 | 200 | 25 | 25 days | 64 |
| 11.5 | 200 | 25 | 60 days | 51 |
| 11.5 | 200 | 5 | 90 days | 93 |
| 11.5 | 200 | 5 | 180 days | 92 |
| 12.5 | 200 | 40 | 4 days | 77 |
| 12.5 | 200 | 25 | 10 days | 94 |
| 12.5 | 200 | 25 | 32 days | 86 |
| 12.5 | 200 | 25 | 60 days | 74 |
| 12.5 | 200 | 5 | 90 days | 99 |
| 12.5 | 200 | 5 | 180 days | 97 |
| 13.0, Batch #1 | 200 | 40 | 4 days | 85-86 |
| 13.0, Batch #1 | 200 | 25 | 18 days | 96 |
| 13.0, Batch #1 | 200 | 25 | 36 days | 82 |
| 13.0, Batch #1 | 200 | 25 | 60 days | 74 |
| 13.0, Batch #1 | 200 | 5 | 90 days | 99 |
| 13.0, Batch #1 | 200 | 5 | 180 days | 98 |
| 13.0, Batch #1 | 200 | 5 | 270 days | 95 |
| 13.0, Batch#2 | 200 | 25 | 18 days | 96 |
| 13.0, Batch#2 | 200 | 25 | 36 days | 82 |
| 13.0, Batch#2 | 200 | 25 | 90 days | 75 |
| 13.0, Batch#2 | 200 | 5 | 90 days | 100 |
| 13.0, Batch#2 | 200 | 5 | 180 days | 97 |
| 13.0, Batch#2 | 200 | 5 | 270 days | 95 |
| 13.0, batch #3 | 200 | 25 | 18 days | 97 |
| 13.0, batch #3 | 200 | 25 | 36 days | 82 |
| 13.0, batch #3 | 200 | 25 | 90 days | 76 |
| 13.0, batch #3 | 200 | 5 | 90 days | 101 |
| 13.0, batch #3 | 200 | 5 | 180 days | 97 |
| 13.0, batch #3 | 200 | 5 | 270 days | 95 |

*Further analysis discontinued due to crystals formation

As can be seen from the table above, the stability of amifostine solutions was substantially maintained for extended periods of time when the amifostine was kept under refrigerated conditions and in a solution having a pH of 10 or higher. Indeed, there was only about an 8 to 10% loss at 5° C., after 180-day storage at pH's ranging from 10 to 11.5, while pH 12.5 and 13 formulations showed a potency loss of 3% or less under the same conditions. These data demonstrate that the free base form of amifostine is surprisingly quite stable at pH 12.5 and above.

It should be further understood from the data that pH's and temperature ranges around the exact data points are expected to behave similarly. Thus, formulations having a pH of 10 or 10.7 kept under refrigerated conditions within the ranges described herein are also within the scope of the invention and will have the extended storage stability demonstrated herein.

I claim:

1. A refrigeration storage stable concentrated aqueous liquid concentrate amifostine formulation comprising an initial amount of amifostine or a pharmaceutically acceptable salt thereof and water at a pH of at least 12.5 whereby said amifostine is present in solution as an amifostine moiety having a net negative charge, and wherein said formulation has a storage stability of such at least 95% of the initial amount of the amifostine remains when stored for a period of 90 days under refrigeration, said refrigeration being at a temperature of about 2° C. to about 8° C.

2. The formulation of claim 1 wherein said initial amount of amifostine is present in a concentration of from about 50 mg/ml to about 250 mg/ml.

3. The formulation of claim 2 wherein said initial amount of amifostine is about 200 mg/ml.

4. The formulation of claim 1 consisting of amifostine or a pharmaceutically acceptable salt thereof, water, and optionally a pH adjuster to adjust said pH to at least 12.5.

5. The formulation of claim 1 consisting essentially of amifostine or a pharmaceutically acceptable salt thereof, water, and optionally a pH adjuster to adjust said pH to at least 12.5.

6. The formulation of claim 1 wherein said amifostine has a net charge of about −2.

7. A method of stably storing an amifostine concentrate aqueous solution of claim 1 comprising dissolving an amifostine compound in an aqueous pharmaceutically acceptable liquid carrier at a pH of at least 12.5 and refrigerating said solution.

8. A method of preparing an IV injectable preparation of amifostine comprising diluting the formulation of claim 1 in an IV injectable diluent to a final concentration of from about 5 mg/ml to about 40 mg/ml and an IV injectably compatible pH.

9. A kit comprising the refrigeration storage stable concentrated aqueous liquid concentrate amifostine formulation of claim 1, a pharmaceutically acceptable container and instructions for long term storage under refrigerated conditions.

10. A method of making a refrigeration storage stable concentrated aqueous liquid concentrate amifostine formulation of claim 1 comprising obtaining an aqueous solution of amifostine or a salt thereof, said solution having an initial pH, adjusting said initial pH to a pH of at least 12.5.

11. A method of treating an amifostine responsive condition in a patient in need thereof comprising administering to said patient an effective amount of amifostine obtained from the formulation of claim 1.

\* \* \* \* \*